United States Patent
Senior et al.

(10) Patent No.: US 10,195,345 B2
(45) Date of Patent: Feb. 5, 2019

(54) DEDICATED CARTRIDGE

(75) Inventors: James Senior, Warwickshire (GB); James Alexander Davies, Warwickshire (GB)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 1135 days.

(21) Appl. No.: 13/992,327

(22) PCT Filed: Dec. 21, 2011

(86) PCT No.: PCT/EP2011/073498
§ 371 (c)(1),
(2), (4) Date: Jun. 7, 2013

(87) PCT Pub. No.: WO2012/085017
PCT Pub. Date: Jun. 28, 2012

(65) Prior Publication Data
US 2013/0253433 A1    Sep. 26, 2013

Related U.S. Application Data

(60) Provisional application No. 61/425,932, filed on Dec. 22, 2010.

(30) Foreign Application Priority Data

Mar. 8, 2011    (EP) .................................. 11157373

(51) Int. Cl.
*A61M 5/31*    (2006.01)
*A61M 5/24*    (2006.01)
*A61M 5/34*    (2006.01)

(52) U.S. Cl.
CPC ................ *A61M 5/31* (2013.01); *A61M 5/24* (2013.01); *A61M 5/347* (2013.01);
(Continued)

(58) Field of Classification Search
CPC .. A61M 2005/2411; A61M 2005/2437; A61M 2005/2444; A61M 2005/6045;
(Continued)

(56) References Cited

U.S. PATENT DOCUMENTS

| 533,575 | A |  | 2/1895 | Wilkens |
| 4,643,724 | A | * | 2/1987 | Jobe ........................ A61M 5/24 604/232 |

(Continued)

FOREIGN PATENT DOCUMENTS

| EP | 0937471 | 8/1999 |
| EP | 0937476 | 8/1999 |

(Continued)

OTHER PUBLICATIONS

International Search Report for Int. App. No. PCT/EP2011/073498, completed Oct. 17, 2012.

*Primary Examiner* — Kevin C Sirmons
*Assistant Examiner* — Leah Swanson
(74) *Attorney, Agent, or Firm* — Fish & Richardson P.C.

(57) ABSTRACT

A cartridge assembly for use with a drug delivery device is specified. The cartridge assembly comprises a cartridge with a retention cap and a cartridge holder. According to one aspect, the cartridge and the cartridge holder may be configured to be fixed to each other in a predetermined position According to another aspect, the retention cap comprises at least one coding feature configured to affix said cartridge to said cartridge holder in the predetermined position by the mating of said coding feature with a corresponding coding feature on the cartridge holder.

16 Claims, 6 Drawing Sheets

(52) U.S. Cl.
CPC ............. *A61M 2005/2411* (2013.01); *A61M 2005/2414* (2013.01); *A61M 2005/2437* (2013.01); *A61M 2005/2444* (2013.01); *A61M 2205/6045* (2013.01)

(58) Field of Classification Search
CPC ............. A61M 5/31; A61M 5/347; A61M 2005/2407; A61M 2005/2414; A61M 2005/2433; A61M 2005/244; A61M 2005/2485; A61M 2005/2488; A61M 2005/2492; A61M 2005/2496
See application file for complete search history.

(56) References Cited

U.S. PATENT DOCUMENTS

| | | | |
|---|---|---|---|
| 5,112,307 A * | 5/1992 | Haber | A61M 5/24 604/110 |
| 5,226,895 A | 7/1993 | Harris | |
| 5,279,586 A | 1/1994 | Balkwill | |
| 5,304,152 A | 4/1994 | Sams | |
| 5,320,609 A | 6/1994 | Haber et al. | |
| 5,330,450 A * | 7/1994 | Lopez | A61M 39/04 604/284 |
| 5,360,409 A * | 11/1994 | Boyd, III | A61M 5/24 604/198 |
| 5,383,865 A | 1/1995 | Michel | |
| 5,480,387 A | 1/1996 | Gabriel et al. | |
| 5,505,704 A | 4/1996 | Pawelka et al. | |
| 5,549,575 A * | 8/1996 | Giambattista | A61M 5/24 604/206 |
| 5,569,214 A * | 10/1996 | Chanoch | A61M 5/31566 604/207 |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,693,027 A | 12/1997 | Hansen et al. | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,017,330 A * | 1/2000 | Hitchins | A61M 5/14546 604/131 |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,752,798 B2 * | 6/2004 | McWethy | A61M 5/3257 222/327 |
| 6,899,698 B2 | 5/2005 | Sams | |
| 6,936,032 B1 | 8/2005 | Bush, Jr. et al. | |
| 7,241,278 B2 | 7/2007 | Moller | |
| 2002/0052578 A1 | 5/2002 | Moller | |
| 2002/0120235 A1 | 8/2002 | Enggaard | |
| 2002/0173748 A1 | 11/2002 | McConnell et al. | |
| 2003/0050609 A1 | 3/2003 | Sams | |
| 2003/0078195 A1 * | 4/2003 | Kristensen | A61M 5/24 604/201 |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0027233 A1 * | 2/2006 | Zierenberg | A61M 11/06 128/200.21 |
| 2006/0153693 A1 | 7/2006 | Fiechter et al. | |
| 2009/0275916 A1 | 11/2009 | Harms et al. | |
| 2009/0299328 A1 | 12/2009 | Mudd et al. | |

FOREIGN PATENT DOCUMENTS

| | | |
|---|---|---|
| EP | 1731187 | 12/2006 |
| WO | 95/18644 | 7/1995 |
| WO | 99/16487 | 4/1999 |
| WO | 99/38554 | 8/1999 |
| WO | 01/10484 | 2/2001 |
| WO | 2005/077441 | 8/2005 |
| WO | 2009/124407 | 10/2009 |
| WO | 2010/006870 | 1/2010 |
| WO | WO 2010006870 A1 * | 1/2010 |
| WO | 2011/131779 | 10/2011 |

* cited by examiner

DEDICATED CARTRIDGE

CROSS REFERENCE TO RELATED APPLICATIONS

The present application is a U.S. National Phase Application pursuant to 35 U.S.C. § 371 of International Application No. PCT/EP2011/073498 filed Dec. 21, 2011, which claims priority to U.S. Provisional Patent Application No. 61/425,932 filed Dec. 22, 2010 and European Patent Application No. 11157373.9 filed Mar. 8, 2011. The entire disclosure contents of these applications are herewith incorporated by reference into the present application.

FIELD OF DISCLOSURE

The present patent application is generally directed to reservoirs, particularly reservoirs containing a medicament. More particularly, the present application is generally directed to a coding mechanism for use with a reservoir and a reservoir holder so as to ensure the reservoir and reservoir holders are only used with the drug for which they are intended. As just one example, such medicament reservoirs may comprise an ampoule, a cartridge, a vial, or a pouch, and may be used with a medical delivery device. Exemplary medical delivery devices include, but are not limited to syringes, pen type injection syringes, pumps, inhalers, or other similar injection or infusing devices that require at least one reservoir containing at least one medicament.

BACKGROUND

Medicament reservoirs such as ampoules, cartridges, or vials are generally known. Such reservoirs are especially used for medicaments that may be self administered by a patient. For example, with respect to insulin, a patient suffering from diabetes may require a certain amount of insulin to either be injected via a pen type injection syringe or infused via a pump. With respect to certain known reusable pen type drug delivery devices, a patient loads a cartridge containing the insulin into a proximal end of a cartridge holder. After the cartridge has been correctly loaded, the user may then be called upon to select a dose of medicament. Multiple doses may be dosed from the cartridge. Where the drug delivery device comprises a reusable device, once the cartridge is empty, the cartridge holder is disconnected from the drug delivery device and the empty cartridge is removed and replaced with a new cartridge. Most suppliers of such cartridges recommend that the user dispose of the empty cartridges properly. Where the drug delivery device comprises a disposable device, once the cartridge is empty, the user is recommended to dispose of the entire device.

Such known self administration systems requiring the removal and reloading of empty cartridges have certain limitations. For example, in certain generally known systems, a user simply loads a new cartridge into the delivery system without the drug delivery device or without the cartridge having any mechanism of preventing removal and subsequent cross use of an incorrect cartridge. Alternatively, certain known drug delivery devices do not present a mechanism for determining if the correct type of medicament within the cartridge should be used with that particular drug delivery system. This potential problem could be exacerbated given that certain elderly patients, such as those suffering from diabetes, may have limited manual dexterity. Identifying an incorrect medicament is quite important, since the administration of a potentially incorrect dose of a medicament such as a short acting insulin in lieu of a long insulin could result in injury or even death.

Some drug delivery devices or systems may use a color coding scheme to assist a user or care giver in selecting the correct cartridge to be used with a drug delivery device. However, such color coding schemes pose challenges to certain users, especially those users suffering from poor eyesight or color blindness: a situation that can be quite prevalent in patients suffering from diabetes.

Another concern that may arise with such disposable cartridges is that these cartridges are manufactured in essentially standard sizes and must comply with certain recognized local and international standards. Consequently, such cartridges are typically supplied in standard sized cartridges (e.g., 3 ml cartridges). Therefore, there may be a variety of cartridges supplied by a number of different suppliers and containing different medicament but they may fit a single drug delivery device. As just one example, a first cartridge containing a first medicament from a first supplier may fit a medical delivery device provided by a second supplier. As such, a user might be able to load and then dispense an incorrect medicament (such as a rapid or basal type of insulin) into a drug delivery device without being aware that the medical delivery device was perhaps neither designed nor intended to be used with such a cartridge.

As such, there is a growing desire from users, health care providers, care givers, regulatory entities, and medical device suppliers to reduce the potential risk of a user loading an incorrect drug type into a drug delivery device. There is also, therefore, a desire to reduce the risk of dispensing an incorrect medicament (or the wrong concentration of the medicament) from such a drug delivery device.

Similarly, there is also a general need for a dedicated cartridge that allows the medical delivery device to be used with an authorized cartridge containing a specific medicament while also preventing undesired cartridge cross use.

There is also a general need to provide a dedicated cartridge that is difficult to tamper with so that the cartridge may not be compromised in that the cartridge can be used with an unauthorized drug or drug delivery device. Because such cartridges may be difficult to tamper with, they may also reduce the risk of counterfeiting: i.e., making it more difficult for counterfeiters to provide unregulated counterfeit medicament carrying products.

SUMMARY

The problem to be solved by the present disclosure is to provide a cartridge assembly for a drug delivery device which is particularly safe to use.

According to one aspect, a cartridge—in particular a cartridge for a drug delivery device—is provided for. The cartridge in particular has a proximal end and a distal end.

The cartridge may be physically dedicated, in particular it may be mechanically coded. For example, the cartridge is physically dedicated or mechanically coded to its drug type. In one embodiment the cartridge comprises at least one physical dedication or mechanical coding feature, which is also sometimes denoted as cartridge coding feature in the present disclosure. For example, the cartridge has at least one pair of coding features.

In one embodiment, the cartridge comprises a main body and a retention cap.

The main body may comprise a generally tubular barrel, for example. A distal end of the barrel may, for example, be defined by an inwardly converging shoulder. At the distal end, the main body may include neck which projects distally from the shoulder of the barrel. The neck in particular has a smaller diameter than the barrel. In one development, the smaller diameter neck is provided with a flange, such as an annular bead. The flange in particular extends circumferentially thereabout at the distal end of the neck. The flange in particular has a larger diameter than the neck.

In one embodiment, a seal—which is in particular a septum—is securely mounted across the open distal end of the cartridge, in particular of the main body, the distal end in particular being defined by the neck. The seal is preferably a pierceable seal. The seal may be held in place by a sleeve such as a ferrule. The sleeve may be a metallic sleeve or ferrule. This sleeve may be crimped around the circumferential bead at the distal end of the neck in one development.

The retention cap may be integrally formed with the main body, for example it may be molded as part of the main body. In one development, the retention cap is a separate piece. A retention cap which is a separate piece is preferably mechanically stably secured to the main body. For example, the retention cap is formed such that it mechanically interacts with the main body, in particular with the neck and with the flange and/or sleeve, for preventing axial movement or axial and rotational movement of the main body with respect to the retention cap. In one development, a form-fit or positive-fit connection, in particular a snap-fit connection, is established between the retention cap and the main body.

The retention cap in particular covers the neck, the flange, the sleeve, and/or the seal at least in regions. For example, the retention cap completely surrounds the flange, the seal and the sleeve in a ring-like fashion in top view onto the distal end of the cartridge, such that, in particular, at least a central region of the seal is exposed by the retention cap. In a side view of the cartridge, the retention cap may overlap the flange, the sleeve, the seal and the neck at least in regions. In one embodiment, the retention cap projects distally beyond the main body, and in particular beyond the seal. In another embodiment, the retention cap additionally or alternatively projects proximally beyond the flange.

In one advantageous embodiment, the cartridge coding feature is provided on the retention cap. For example, the proximal end of the retention cap is provided with the cartridge coding feature. In one development, the proximal end of the retention cap which carried the cartridge coding feature overlaps with the barrel part of the main body in a side view of the cartridge.

In one development, the cartridge—in particular the retention cap—has a connection mechanism for connecting a needle assembly to the cartridge. The needle assembly in particular comprises a needle and is configured such that the needle pierces the seal when the needle assembly is connected to the connection mechanism. The needle may be a double ended needle, having a proximal end for piercing the seal and a distal end for dispensing the medicament.

The connection mechanism may comprise a thread, a snap lock, a snap fit, a form fit, or a bayonet lock mechanism, for example. For example, the distal end of the retention cap is provided with the connection mechanism.

According to a further aspect, a cartridge holder, in particular for a drug delivery device such as an injection device, is specified. In particular the cartridge holder may be designed for being connected with a drug delivery mechanism. The drug delivery mechanism acts to expel drug from the cartridge arranged in the cartridge holder. In one embodiment, the cartridge holder is permanently fixed to a drug delivery device. In another embodiment, the cartridge holder is designed for being removably connected to a drug delivery device. The cartridge assembly may in particular be suitable for cooperation with a drug delivery mechanism thereby forming a hand-held device which may be portable by single persons and are operated by using one or two hands. Mobile operation may be the standard application of such a device. The cartridge holder may extend substantially from one end of the cartridge to the other end.

The cartridge holder in particular accepts or works with the dedication or coding feature(s) provided on or with the cartridge. For example, the cartridge holder may have a corresponding physical dedication feature or mechanical coding feature, sometimes also denoted as cartridge holder coding feature in the present disclosure. For example, the cartridge holder has a pair of coding features.

In one embodiment, the cartridge holder has a base which is, in particular, arranged at a proximal end of the cartridge holder. A main body of the cartridge holder may extend from the base, in particular in a distal direction.

According to a further aspect, a cartridge assembly for a drug delivery device is specified. The cartridge assembly comprises the cartridge and the cartridge holder. The cartridge assembly is in particular configured to attach to the drug delivery device, for example to attach to a dose setting mechanism of the drug delivery device.

The cartridge and the cartridge holder may be configured such that they can be fixed in a predetermined position with respect to each other. The cartridge assembly may be provided with a locking mechanism such as a screw connection, a snap lock or bayonet lock for retaining the cartridge assembly in the predetermined position. Here, the term "predetermined position" may in particular refer to a predetermined rotational position, i.e. that the cartridge can be fixed to the cartridge holder in only in the predetermined rotational position with respect to the main longitudinal axis of the cartridge. The term "predetermined position" may in furthermore refer to a specific number of predetermined rotational positions, in particular a number of one or two positions which are predetermined and which are the only rotational positions in which the cartridge can be fixed to the cartridge holder with respect to the main longitudinal axis of the cartridge. Hence, the cartridge assembly may be provided with a locking mechanism such as a screw connection, a snap lock or bayonet lock for retaining the cartridge assembly in one chosen out of one or two predetermined positions.

The predetermined position may for example be an assembled position of the cartridge assembly. In particular, the drug delivery device may be operable to dispense the drug contained in the cartridge when the cartridge assembly is in the assembled position.

The cartridge coding feature and the corresponding cartridge holder coding feature may in particular be configured such that the cartridge coding feature mates with the cartridge holder coding feature when the cartridge and the cartridge holder are in the predetermined position. Again the term "predetermined position" may in particular refer to a predetermined rotational position, i.e. that the cartridge can be fixed to the cartridge holder in only in the predetermined rotational position with respect to the main longitudinal axis of the cartridge. The term "predetermined position" may in furthermore refer to a specific number of predetermined rotational positions, in particular a number of one or two positions which are predetermined and which are the only rotational positions in which the cartridge can be positioned to the cartridge holder with respect to the main longitudinal axis of the cartridge. Hence, the cartridge coding feature and the corresponding cartridge holder coding feature may in particular be configured such that the cartridge coding feature mates with the cartridge holder coding feature only when the cartridge and the cartridge holder are in one chosen out of one or two predetermined positions. In one development, the cartridge coding feature and the corresponding cartridge holder coding feature are configured to fix the cartridge assembly in the assembled position. In particular, the corresponding coding features form the locking mechanism of the cartridge assembly.

In one embodiment, the main body of the cartridge may be positionally fixed with respect to axial movement or with respect to axial and rotational movement by means of mechanical interaction of the retention cap with the cartridge holder. The retention cap and the cartridge holder may be formed such that the main body of the cartridge is received and securely maintained, for example by a form-fit connection, in an inner cartridge cavity formed by the retention cap and the cartridge holder, when the cartridge assembly is the assembled position. For example, the cartridge coding feature is comprised by the retention cap and the retention cap mechanically interacts with the cartridge holder coding feature via the cartridge coding feature to form the locking mechanism, such that the retention cap and the cartridge holder are positionally fixed with respect to each other when the cartridge assembly is in the assembled position.

By means of the cartridge, the cartridge holder and/or the cartridge assembly, the risk of unwanted cartridge cross use for different drug delivery devices is particularly low, for example.

In one embodiment, the cartridge coding feature and the cartridge holder coding feature are configured to affix said cartridge to said cartridge holder by the mating of said coding feature with said corresponding coding feature. Thus, the cartridge and the cartridge holder are, in particular, held in the predetermined position by interaction of the mating coding features.

In one embodiment, the cartridge assembly comprises a snap lock for attachment of the cartridge to the cartridge holder. The snap lock may comprise at least one clip and/or at least one snap. Expediently, the cartridge assembly is designed such that the snap lock is in the locked position when the cartridge assembly is in the predetermined, assembled position.

In one development, the clip has a fixed end which is positionally fixed with respect to the cartridge, in particular with respect to the retention cap and/or with respect to the main body of the cartridge. The clip additionally has a free end that may be radially and/or axially displaceable with respect to the main body and/or the retention cap of the cartridge. In particular, it is displaceable in a reversible, flexible fashion with respect to the main body and/or the retention cap. For example, the clip extends in an axial direction and has a fixed distal end and a free proximal end. The free end of the clip in particular carries a flange, for example a protrusion such as a tooth or nose. For example in case of a radially displaceable clip, the flange may protrude radially inwardly from the clip in one embodiment.

In one configuration, the clip is comprised by the cartridge, in particular on the retention cap. For example in this configuration, the cartridge holder may comprise an aperture within which the protrusion on the clip fits to retain the cartridge in the predetermined position with respect to the cartridge holder. The aperture represents in particular a snap and forms a snap lock together with the clip.

In an alternative configuration, the clip is comprised by the cartridge holder. In this configuration, the cartridge preferably comprises a snap. the snap may, for example, be in form of a lug or strap having a recess which is operable to receive the flange of the corresponding clip.

In one embodiment, the cartridge is provided with the clip and the cartridge coding feature is in the form of a shoulder provided on the clip. For example, the clip has a fixed end that has a greater width than the free end to form the shoulder. The corresponding cartridge holder coding feature may be a recess or cut-out in the cartridge holder. The recess is preferably sized and shaped to correspond with the dimensions of the shoulder. The cartridge assembly may be designed such that the shoulder is positioned in the recess when the cartridge assembly is in the assembled configuration or position.

In another embodiment, the cartridge holder coding feature additionally or alternatively comprises a plurality of indents and protrusions. The indents and protrusions are, in particular, arranged at the distal end of the cartridge holder. The cartridge may have a coding feature in form of corresponding indents and protrusions. The indents and protrusions of the cartridge coding feature may be arranged such that each protrusion of the cartridge coding feature is in engagement with a corresponding indent of the cartridge holder coding feature and each protrusion of the cartridge holder coding feature is in engagement with a corresponding indent of the cartridge coding feature when the cartridge assembly is in the predetermined position.

In one embodiment, the cartridge coding feature or the cartridge holder coding feature comprises one of a snap or a clip. For example, the cartridge coding feature comprises at least one pair of snaps and the cartridge holder coding feature comprises at least one pair of clips corresponding to the snaps. In one development, the snaps and clips, respectively, of each pair have mutually different widths and/or lengths. In this way, a cartridge having such snaps can be only fixed in the predetermined position if the cartridge assembly has a holder with appropriately sized clips.

In another embodiment, the cartridge holder has at least one clip and the cartridge holder coding feature is provided on the clip. For example, the interior surface of the clip comprises the coding feature. In one configuration, the coding feature is comprised by the free end of the clip. The cartridge may have at least one corresponding snap carrying the cartridge coding feature. Alternatively, the cartridge may have the clip provided with the cartridge coding feature and the cartridge holder may comprise the snap carrying the cartridge holder coding feature.

The cartridge coding feature and the cartridge holder coding feature may be provided as corresponding protrusion(s) and indent(s). A snap lock is in particular formed by the clip and snap carrying the respective coding features of the cartridge and the cartridge holder. When the snap lock is in the locked position, the corresponding indents and protrusions of the coding features are in engagement with each other. Thus, the snap lock can only be brought in the locked position, in which locked position the cartridge is attached to the cartridge holder—preferably in a removable fashion—if the coding features of cartridge and cartridge holder match.

In one embodiment of the cartridge assembly, the cartridge is axially insertable into an aperture at a distal end of the cartridge holder.

In one development, the complete cartridge or at least a part of the cartridge, in particular a proximal part of the cartridge is configured to be received in an inner cartridge cavity of the cartridge holder through the aperture. The cartridge assembly may be in the predetermined or assembled position, when the cartridge or the part of the cartridge, respectively, is received in the inner cartridge cavity. The cartridge, in particular its main body, and the inner cartridge cavity may have basically the same cross-sectional shape and size, such that the cartridge preferably can axially slide within the cavity. Expediently, the cartridge coding feature mates with the cartridge holder coding feature when the cartridge or the part of the cartridge is received in the inner cartridge cavity.

In this way, the cartridge fits within the cartridge holder, such that, in particular, the cartridge and the cartridge holder are in the predetermined position. If a cartridge without the cartridge coding feature is inserted into the cartridge holder, the cartridge holder coding feature may be operable to block axial movement of that cartridge, such that the cartridge without the cartridge coding feature cannot be brought into the predetermined position.

In a further development of the cartridge assembly the cartridge can subsequently be removed from the cartridge holder by means of a pulling or pushing force. In one configuration, the cartridge assembly is designed such that the cartridge slips through the distal end of the cartridge holder when being removed from the cartridge holder. In another configuration, the cartridge is removable from the cartridge holder in a proximal direction, such that the cartridge slips through the proximal end of the cartridge holder, opposite of the distal end, when being removed from the cartridge holder. In one development, when a pulling or pushing force is applied for removal of the cartridge from the cartridge holder, the snap feature, i.e. the snap lock, slides out of its attachment position which is also denoted as the locked position in this disclosure.

In another development, the cartridge assembly is designed such that the proximal end of the cartridge can be axially inserted into said cartridge holder—in particular into a main body of the cartridge holder—until the proximal end rests on top of the base of the cartridge holder. The base may limit proximal axial movement of the cartridge with respect to the cartridge holder in this way. In one development, the cartridge assembly is designed such that, after the cartridge is fully inserted into the cartridge holder, the cartridge coding feature is rotatable to fit within the cartridge holder coding feature, attaching the cartridge to the cartridge holder. A bayonet lock may in particular be formed between the cartridge and the cartridge holder by the mating coding features in this way.

In a different embodiment, the cartridge is obliquely or radially inserted into the cartridge holder.

For example, the cartridge holder comprises a main body extending from a base. The main body may have an arc shape, in particular as viewed along a longitudinal axis of the cartridge holder. The arc-shaped cross-section may have a U-shape or a V-shape, for example. Preferably, the main body has an inner surface facing a longitudinal axis of the cartridge holder. The inner surface preferably has the negative general shape of a subregion of the cartridge surface. In this way, the cartridge surface may reside against the inner surface and, in particular, basically the complete inner surface may abut the cartridge surface. The cartridge assembly is preferably in the predetermined position when the cartridge resides against the inner surface of the main body of the cartridge holder. In one embodiment, the cartridge is obliquely inserted into the cartridge holder by placing a proximal end of the cartridge on the base and pressing the cartridge against the main body.

Preferably, when the cartridge is pressed against the arc shaped main body, the cartridge coding feature mates with the cartridge holder coding feature. The cartridge coding feature and the cartridge holder coding feature may in particular interact to hold the cartridge assembly in the assembled position. In this way, the cartridge and the cartridge holder may for example be fixed, in particular releasably fixed, to each other.

In one embodiment, the cartridge assembly comprises a lid, for example a removable cap. The lid is, for example, provided for protecting a dispensing end, in particular the distal end, of the cartridge when the drug delivery device is not in use. The lid may have an aperture such as a window or a cut-out which exposes a subregion of the cartridge when the lid is placed over the cartridge. For example, the cartridge comprises a clip, and the lid is designed such that the clip remains visible when the lid is placed over the cartridge. The exposed subregion—for example the clip—may be color coded and/or comprise written information in one development. Thus, visual drug differentiation can be provided even when the drug delivery device is fully assembled.

According to an exemplary embodiment, a cartridge assembly for use with a drug delivery device is provided. The cartridge assembly comprises a cartridge holder and a cartridge with a retention cap. The retention cap comprises at least one coding feature configured to affix the cartridge to the cartridge holder by mating with a corresponding coding feature on the cartridge holder.

In an alternative arrangement, a cartridge assembly for use with a drug delivery device is provided. The cartridge assembly comprises a cartridge holder with at least one coding feature and a cartridge. The cartridge comprises a distal end, a proximal end, and at least one coding feature. The distal end of the cartridge is inserted into the cartridge holder. When the cartridge coding feature mates with the cartridge holder coding feature, the cartridge is allowed to fit within the cartridge holder.

In the following text, further aspects of the present disclosure are specified. The individual aspects are enumerated in order to facilitate the reference to features of other aspects.

1. A cartridge assembly for use with a drug delivery device, wherein the cartridge assembly is configured to attach to a drug delivery device, the cartridge assembly comprising:
   a cartridge holder; and
   a cartridge with a retention cap;
   wherein said retention cap comprises at least one coding feature configured to affix said cartridge to said cartridge holder by the mating of said coding feature with a corresponding coding feature on said cartridge holder.
2. The cartridge assembly of aspect 1 wherein said cartridge is axially inserted into an aperture at a distal end of said cartridge holder.
3. The cartridge assembly of aspect 1 wherein said retention cap comprises a clip, and wherein when a lid is placed over said cartridge said clip remains visible.
4. The cartridge assembly of aspect 3 wherein said cartridge holder comprises an aperture within which a protrusion on said clip fits to retain said cartridge within said cartridge holder.
5. The cartridge assembly of aspect 1 wherein said at least one coding feature is a pair of coding features, and wherein said coding features comprise a snap.
6. The cartridge assembly of aspect 5 wherein said cartridge holder comprises a pair of clips, the interior surface of said clips comprising coding features.
7. The cartridge assembly of aspect 6 wherein when said cartridge is axially inserted into a distal end of said cartridge holder, said cartridge coding features mate with said clip coding features, and wherein said snap attaches said cartridge to said cartridge holder.
8. The cartridge assembly of aspect 2 wherein said coding features comprise a plurality of indents and protrusions at said distal end of said cartridge holder.
9. The cartridge assembly of aspect 7 wherein said cartridge is removable from said cartridge holder.
10. A cartridge assembly for use with a drug delivery device, wherein the cartridge assembly is configured to attach to a drug delivery device, the cartridge assembly comprising:
a cartridge holder comprising a distal end, a proximal end, and at least one coding feature; and
a cartridge comprising at least one coding feature;
wherein said cartridge is inserted into an aperture at said distal end cartridge holder, and wherein said cartridge coding feature mates with said cartridge holder coding feature, allowing said cartridge to fit within said cartridge holder.
11. The cartridge assembly of aspect 10, wherein said cartridge coding features and said corresponding cartridge holder coding features are radially spaced.
12. The cartridge assembly of aspect 10 wherein said cartridge further comprises a snap feature for attachment of said cartridge within said cartridge holder.
13. The cartridge assembly of aspect 12 wherein said cartridge can subsequently be removed from said cartridge holder by a pulling force removing said cartridge holder from said cartridge, such that said cartridge slips through the proximal end of said cartridge holder.
14. The cartridge assembly of aspect 13 wherein when said force is applied to said cartridge holder, said snap feature of said cartridge slides out of its attachment position.
15. The cartridge assembly of aspect 10 wherein said cartridge holder comprises an arc shaped main body extending from a cylindrical base.
16. The cartridge assembly of aspect 15 wherein said cartridge is obliquely inserted into said cartridge holder by placing a proximal end of said cartridge on said base, and pressing said cartridge against said arc shaped main body.
17. The cartridge assembly of aspect 16 wherein when said cartridge is pressed against said arc shaped main body, said cartridge coding feature mates with said cartridge holder coding feature.
18. The cartridge assembly of aspect 15 wherein a proximal end of said cartridge is axially inserted into said cartridge holder, until said proximal end rests on top of said base.
19. The cartridge assembly of aspect 18 wherein after said cartridge is fully inserted into said cartridge holder, said cartridge coding feature is rotated to fit within said cartridge holder coding feature, attaching said cartridge to said cartridge holder.
20. The cartridge assembly of aspect 12 wherein said cartridge can subsequently be removed from said cartridge holder by a pulling force removing said cartridge holder from said cartridge, such that said cartridge slips through the distal end of said cartridge holder.

The terms "drug", "medicament", and "mediaction", as used in the present disclosure, preferably mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu- Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39), des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

These as well as other advantages of various aspects of the present invention will become apparent to those of ordinary skill in the art by reading the following detailed description, with appropriate reference to the accompanying drawings.

The scope of the invention is in particular defined by the content of the claims. The invention is not limited to specific embodiments but comprises any combination of elements of different embodiments as specified in the description or in the claims. Moreover, the invention comprises any combination of claims and any combination of features disclosed by the claims or in the description.

BRIEF DESCRIPTION OF THE DRAWINGS

Exemplary embodiments are described herein with reference to the schematic drawings, in which.

DETAILED DESCRIPTION

Figure 1:
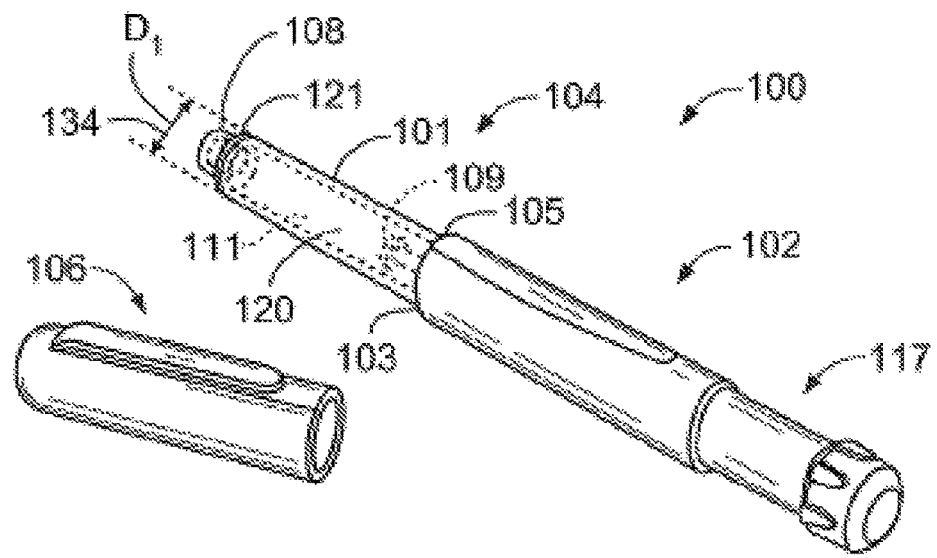
FIG. 1 illustrates an exemplary pen type drug delivery device.

Referring to FIG. 1, there is shown a drug delivery device 100 in the form of a pen type syringe. This drug delivery device 100 comprises a dose setting mechanism 102, a cartridge holder 104, and a removable cap 106. A proximal end 105 of the cartridge holder 104 and a distal end 103 of the dose setting mechanism 102 are removably secured together. The dose setting mechanism 102 comprises a piston rod 109, such as a threaded piston rod that rotates when a dose is injected.

In one exemplary configuration, to inject a previously set dose, a double ended needle assembly may be attached to a distal end 108 of the cartridge holder. Preferably, the distal end of the holder comprises a thread 121 (or other suitable connecting mechanism such as a snap lock, snap fit, form fit, or bayonet lock mechanism) so that the needle assembly may be removably attached to the distal end of the holder. When the drug delivery device is not in use, the removable cap 106 can be releasably retained over the cartridge holder 104.

Figure 2:
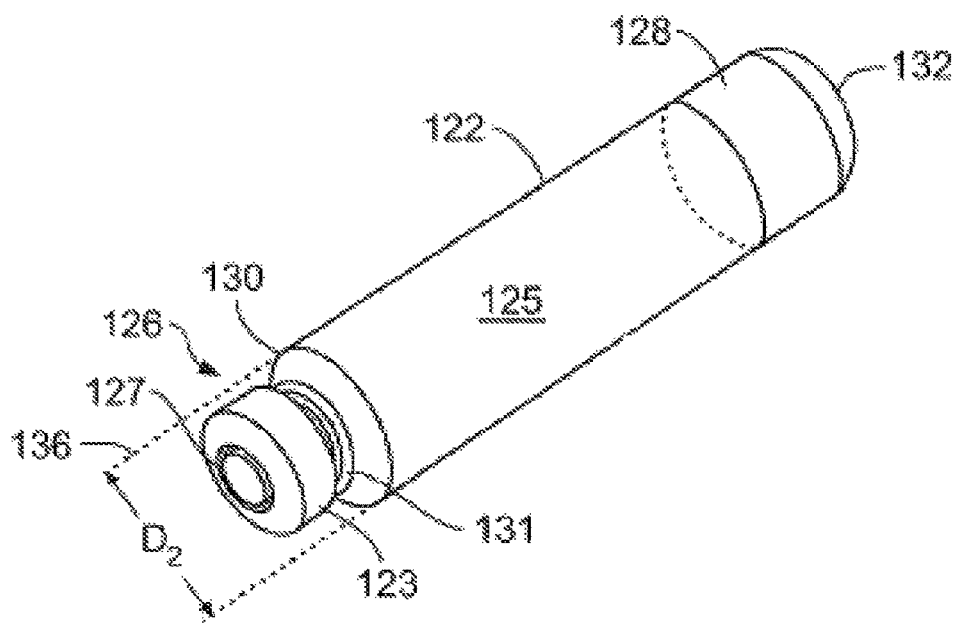
FIG. 2 illustrates a cartridge that may be loaded into a cartridge holder of the pen type drug delivery device illustrated in FIG. 1.

An inner cartridge cavity 111 defined by the cartridge holder 104 is dimensioned and configured to securely receive and retain the cartridge 120. FIG. 2 illustrates a perspective view of the cartridge 120 that may be used with the drug delivery device illustrated in FIG. 1. The cartridge 120 includes a generally tubular barrel 122 extending from a distal end 130 to a proximal end 132. The distal end 130 may, for example, be defined by an inwardly converging shoulder 131.

At the distal end 130, the cartridge 120 includes a smaller diameter neck 126 and this neck projects distally from the shoulder 131 of the barrel 122. Preferably, this smaller diameter neck 126 is provided with a large diameter annular bead (not shown) and this bead extends circumferentially thereabout at the extreme distal end of the neck 126. A pierceable seal or septum 127 is securely mounted across the open distal end defined by the neck. The seal 127 may be held in place by a sleeve or ferrule 123, in particular by a metallic sleeve or ferrule 123. This ferrule 123 may be crimped around the circumferential bead at the distal end of the neck. The diameter of ferrule 123 is shown by $D_2$ 136. The medicament 125 is pre-filled into the cartridge 120 and is retained within the cartridge, in part, by the pierceable seal 127, the metallic sleeve 123, and the stopper 128. The stopper 128, which is sometimes also denoted as piston 128, is in sliding fluid-tight engagement with the inner tubular wall of the barrel 122. Axially directed forces acting upon the stopper 128 during dose injection or dose administration urges the medicament or medication 125 from the cartridge, for example through the double ended needle mounted onto the distal end 130 of the cartridge holder 104 and, in particular, into the injection site. By means of an axially directed force on the stopper 128, the medication 125—also referred to as a drug or a medicament in this disclosure—may also be dispensed from the cartridge at its distal end 130—representing a dispensing end in this case—for testing purposes. Such axial forces may be provided by the piston rod 109.

A portion of the cartridge holder 104 defining the cartridge holder cavity 111 is of substantially uniform diameter represented in FIG. 1 by $D_1$ 134. This diameter $D_1$ is preferably slightly greater than the diameter $D_2$ of the cartridge 120. The interior of the cartridge holder includes an inwardly-extending annual portion or stop that is dimensioned to prevent the cartridge 120 from moving within the cartridge holder 104. For example, the inwardly-extending annular portion or stop is configured to block distal movement of the cartridge with respect to the cartridge holder, when the cartridge is fully loaded in the cartridge holder cavity. In one configuration, the inwardly-extending annular portion or stop may represent a distal end of the cartridge holder cavity. In this manner, when the cartridge 120 is loaded into the cavity 111 of the cartridge holder 104 and the cartridge holder 104 is then connected to the dose setting mechanism 102—the dose setting mechanism sometimes also being denoted as dose setting member 102—the cartridge 120 will be securely held within the cartridge cavity. More particularly, the neck 126 and ferrule 123 of the cartridge 120 are inserted in a proximal to distal direction into the open proximal end of the cartridge holder 104 with the ferrule eventually passing entirely into the holder 104. With the holder 104 removably coupled to the dose setting mechanism 102, the proximal end of the cartridge 120 will typically abut a stop provided by the dose setting member 102.

A number of doses of a medicament 125 may be dispensed from the cartridge 120. Preferably, the cartridge 120 contains a type of medicament that must be administered often, such as one or more times a day. One such medicament is insulin. The stopper 128 is retained in a first end or proximal end of the cartridge 120 and receives an axial force created by the piston rod 109 of the dose setting mechanism 102.

The dose setting mechanism 102 comprises a dose setter 117 at the proximal end of the dose setting mechanism. In one preferred arrangement, the dose setter 117 is rotated to set a dose. To administer this set dose, the user attaches the needle assembly comprising a double ended needle on the distal end of the cartridge holder. In this manner, the needle assembly pierces the seal 127 of the cartridge 120 and is therefore in liquid communication with the medicament 125. The user pushes on the dose setter 117 to inject the set dose. The same dose setting and dose administration procedure is followed until the medicament 125 in the cartridge is expended, at which time a new cartridge may be loaded in the device. To exchange an empty cartridge, the user is called upon to remove the cartridge holder 104 from the dose setting mechanism 102.

Figure 3:
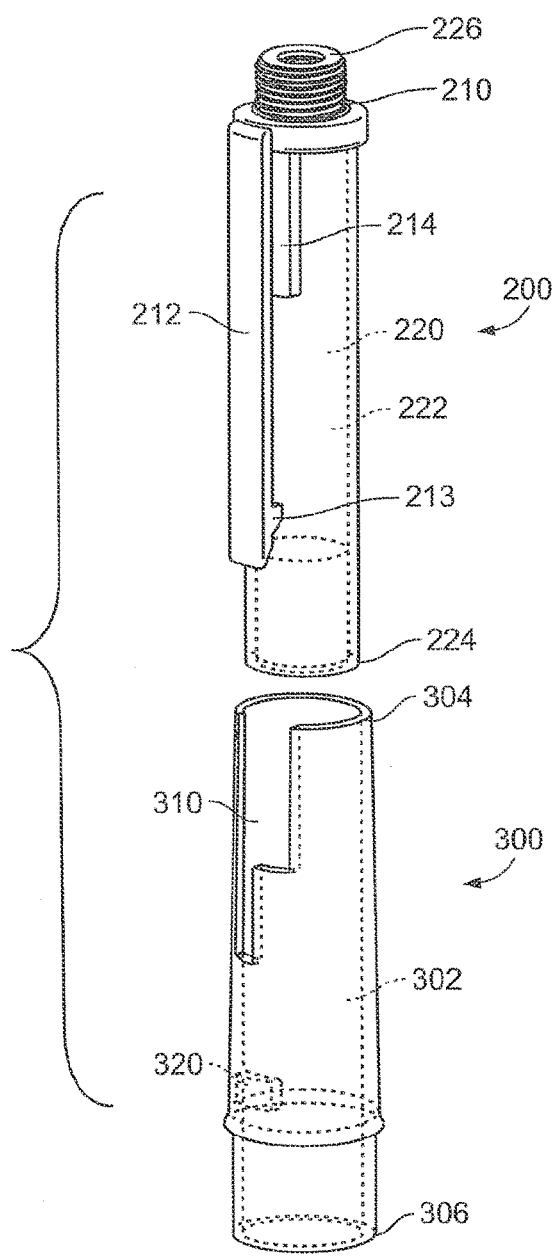
FIG. 3 illustrates a perspective view of an exemplary cartridge and cartridge holder.

FIG. 3 is a perspective view of an exemplary cartridge 200 for use with an exemplary cartridge holder 300. Cartridge 200 and cartridge holder 300 are for use with a pen type drug delivery device, such as drug delivery device 100, cartridge 120, and cartridge holder 104 illustrated in FIGS. 1 and 2.

Cartridge 200 comprises a main body 220 with an exterior surface 222, a distal end 226, and a proximal end 224. The cartridge 200 may be designed in a similar fashion as described above in connection with FIG. 2. In particular, at its distal end 226, the cartridge may comprise at least one of a neck 126, a pierceable seal 127, and a sleeve or ferrule 123.

In the present embodiment, cartridge 200 is fitted with a retention cap 210, in particular at its distal end 226. Retention cap 210 may be a separate piece that is attached to cartridge 200, or may be molded as part of cartridge 200. The neck 126, seal 127 and/or ferrule 123 may be covered by retention cap 210. In top view of the cartridge, the retention cap 210 may expose at least a central part of the seal 127. In one development, retention cap 200 may be provided with a connection mechanism for a needle assembly, such as a thread.

Such a configuration may be particularly useful when retention cap 210 is a separate piece that is attached to the main body 220 of cartridge 200. For example, the retention cap 210 may be attached to the main body by forming a positive-fit connection such as a snap-fit connection between the retention cap 210 and the ferrule 123 of the main body 200.

Retention cap 210 may include one or more clips 212 with a flange 213 and at least one dedication feature such as at least one coding feature 214. Flange 213 may in one configuration protrude from the interior surface of clip 212, that is, from the surface of clip 212 that faces the exterior surface 222 of main body 220 of cartridge 200.

In another exemplary configuration, main body 220 may be provided with the clip(s) 212 and/or coding feature(s) 214. For example, the clip(s) 212 and/or coding feature(s) 214 may be molded with the main body 220.

In the present embodiment, clip 212 has a distal end which is positionally fixed with respect to the retention cap 210 and in particular with the main body 220 of the cartridge 200. A proximal end of the clip 212, which in particular carries the flange 213, may be radially displaceable with respect to the main body 220, in particular in a reversible, flexible fashion.

Flange 213 may be in the form of an inwardly projecting tooth or nose, for example. In one exemplary development, coding feature 214 may be in the form of a shoulder provided on the clip 212.

The coding feature may be a shoulder 214 on the clip 212. For example, the fixed distal end of the clip 212 has a greater width than the free proximal end of the clip 212 to form the shoulder.

Cartridge holder 300 comprises a main body 302, a distal end 304, and a proximal end 306. Cartridge holder 300 also comprises at least one recess 310 that is sized and shaped to correspond with the at least one dedication feature 214, in particular with the coding feature 214 of the cartridge 200. Thus, cartridge holder 300 has a coding feature, represented by the recess 310, corresponding to the coding feature 214 of the cartridge. Cartridge holder 300 may also comprise an aperture 320 within which flange 213 may fit, to better secure clip 212 to cartridge holder 300. Aperture 320 in particular represents a snap.

The coding feature(s) 214 on retention cap 210 serve as a coding mechanism. More specifically, as cartridge 200 is axially inserted into the cartridge holder 300 from the distal end 304 of the holder, coding feature 214 slides within recess 310. If coding feature 214 is not compatible and does not match the shape of recess 310, the cartridge travel will be restricted, and cartridge 200 will not be able to continue to be inserted within cartridge holder 300. If dedication feature 214 does match with recess 310, however, cartridge 200 is able to be fully inserted into cartridge holder 300. When cartridge 200 is fully inserted, flange 213 may be snap-fit into aperture 320, retaining cartridge 200 within cartridge holder 300, in particular in a predetermined, assembled position.

Cartridge 200 may subsequently be removed from holder 300 by disengaging flange 213 from aperture 320. In an alternative embodiment, instead of a flange, another attachment and detachment mechanism may be used. Such a mechanism could be operated by rotating, partially or fully removing holder 300 from the injection device, or by some other means incorporated into the injection device itself.

In this manner, retention cap 210 can provide a coding feature to the cartridge 200 to allow for assembly with a corresponding cartridge holder. If an incorrect cartridge insertion is attempted, the cartridge travel will be restricted and the retention clip will not be able to engage with the holder, preventing the cartridge from being retained within the holder. Thus, no drug can be dispensed.

Figure 4:
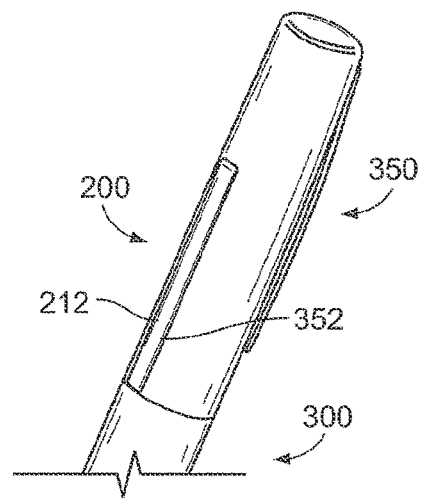
FIG. 4 illustrates a perspective view of the exemplary cartridge and cartridge holder of FIG. 3 with an exemplary cap that may be fitted over the cartridge.

FIG. 4 shows the cartridge 200 of FIG. 3 fully assembled with the cartridge holder 300, wherein a lid 350 has been placed over cartridge 200. Lid 350 comprises a slot 352. When lid 350 is placed over cartridge 200, slot 352 is aligned with clip 212 so that clip 212 fits within slot 352. This way, when lid 350 fully covers cartridge 200, clip 212 remains visible. Clip 212 may be color-coded so as to provide a visual drug differentiation when the medical device is fully assembled. In one exemplary configuration, the lid 350 may be represented by the removable cap 106 of the drug delivery device.

Figure 5:
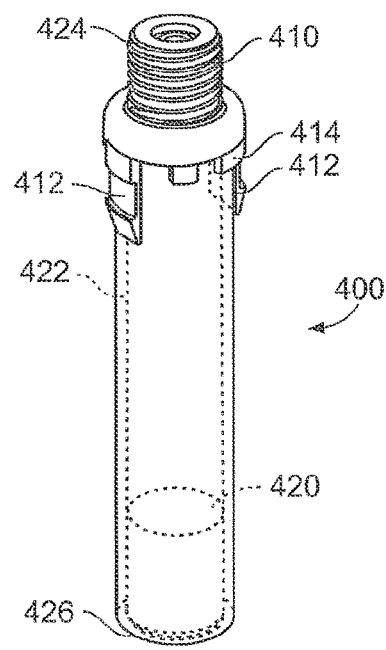
FIG. 5 illustrates a perspective view of an alternative exemplary arrangement of a cartridge.
Figure 6:
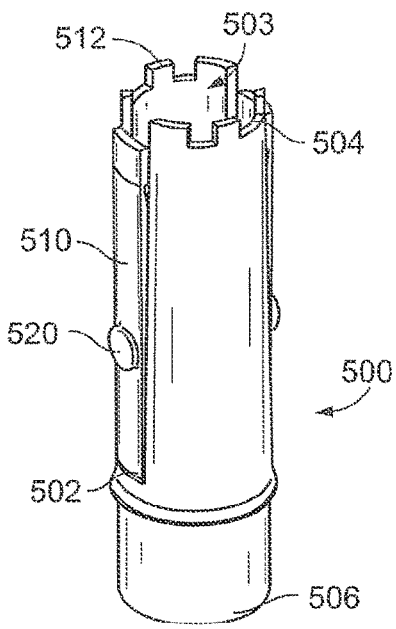
FIG. 6 illustrates a perspective view of an alternative exemplary arrangement of a cartridge holder.

FIG. 5 illustrates a perspective view of an alternative arrangement of a cartridge 400, for use with an alternative arrangement of a cartridge holder 500, which is shown in FIG. 6. Cartridge 400 comprises a main body 420 with an exterior surface 422, a distal end 424, and a proximal end 426. Cartridge 400 is also fitted with a retention cap 410. Retention cap 410 may be a separate piece that is attached to cartridge 400, or may be molded as part of cartridge 400. As shown in FIG. 5, retention cap 410 includes a plurality of snaps 412 (FIG. 5 shows two such snaps) and at least one coding feature 414. Having a plurality of snaps increases the rigidity of the cartridge when retained within a holder during drug delivery.

Coding features 414 may be protrusions, indents, or a combination thereof, at the proximal end of the retention cap 410 which may be provided on the distal end 424 of the cartridge 400. The cartridge coding features 414 may be provided on an exterior surface of the retention cap 410, facing away from the longitudinal axis of the cartridge 400. For example, the cartridge coding features comprise an inclined region of the exterior surface of the retention cap, the inclination angle being such that the distance of the exterior surface from the longitudinal axis increases in the course from the proximal to the distal end of the retention cap. The inclined region may be followed by a step forming one edge of a recess in the exterior surface. By means of such coding features on the exterior surface of the retention cap, a particularly stable mechanical connection of the cartridge to the cartridge holder may be achieved.

Cartridge holder 500 comprises a main body 502 defining an aperture 503, a distal end 504, and a proximal end 506. Cartridge holder 500 also comprises at least one clip 510 (FIG. 6 shows two such clips) and at least one coding feature 512. Coding features 512 may be protrusions, indents, or a combination thereof, at distal end 504. Clips 510 may extend along a significant portion of the length of cartridge holder 500, comprise a portion of the exterior and interior surfaces of cartridge holder 500, and may be made to be flexible such that a user is able to press against each clip 510, flexing the clip inward, in particular flexing the distal end of the clip radially inward. A pad 520 may be present on the exterior of at least one clip 510, in particular of each clip 510, for user facilitation when pressing against the clip. In one configuration, each clip 510 may comprise a flange, such as a nose or tooth, provided for engaging a respective recess of the corresponding snap 412.

The clips 510 may be positioned such that cartridge 400 is forced to travel axially within holder 500 in order to attach to the holder. Alternatively or additionally, the cartridge and the cartridge holder may in one development comprise corresponding guide features such as an axial protrusion and an axial groove or slot provided for forcing the cartridge 400 to travel axially within holder 500 in order to attach to the holder.

The slot may be comprised by the cartridge holder, for example. In particular, the slot precedes one of the clips 510 in an outwardly radial direction. The axial protrusion may be comprised be the cartridge, for example. It may be represented by one of the snaps 412, for example. The snap 412 may slide in the slot when the cartridge 400 travels axially within the holder 500.

By means of the clips and/or the guide features, the cartridge 400 and the cartridge holder 500 may be rotationally locked with respect to each other during axial travel of the cartridge 400 within the holder 500. For example, reproducible and predefined rotational alignment of cartridge 400 and cartridge holder 500 may be achieved in this way.

Figure 7:
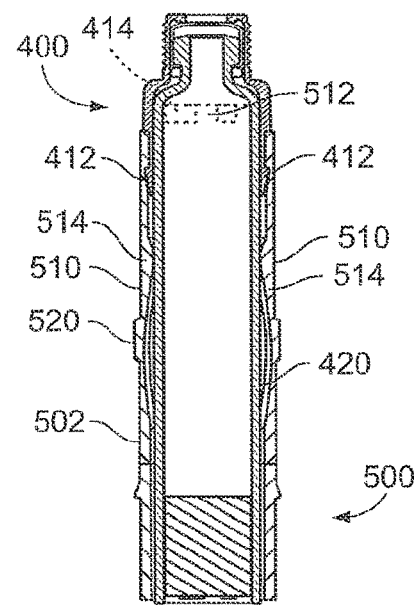
FIG. 7 illustrates a cross-sectional view of the cartridge of FIG. 5 properly affixed within the cartridge of FIG. 6.
Figure 8:
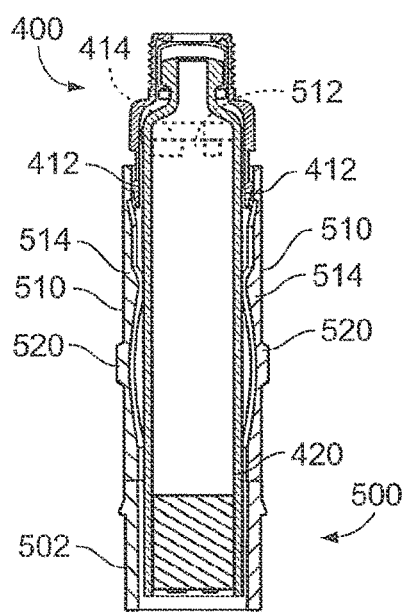
FIG. 8 illustrates a cross-sectional view of an exemplary cartridge such as the cartridge in FIG. 5 that is mis-matched with an improper cartridge holder.

FIGS. 7 and 8 illustrate cross-sectional views of a cartridge and cartridge holder such as the cartridge of FIG. 5 and the cartridge holder of FIG. 6. These cross-sectional views illustrate the interior structure of clips 510 and how clips 510 mate with snaps 412 and coding features 414 mate with coding features 512.

FIG. 7 shows a "pass" configuration, that is, when a correct cartridge and cartridge holder combination are used and the cartridge is allowed to pass through cartridge holder as designed. The indents and protrusions of the cartridge coding feature 414 are in particular arranged such that each protrusion of the cartridge coding feature is in engagement with a corresponding indent of the cartridge holder coding feature 512 and each protrusion of the cartridge holder coding feature 512 is in engagement with a corresponding indent of the cartridge coding feature 414 when the cartridge assembly is in the predetermined, assembled position of the cartridge assembly.

FIG. 8, in contrast, shows the "fail" configuration, which occurs when an incorrect or improper combination is used, and the clips 510 of cartridge holder 500 are unable to engage with snaps 412 of cartridge 400 because coding features 414 do not fit within the coding features 512 on cartridge holder 500.

The coding features 414 serve as coding mechanisms. More specifically, as cartridge 400 is axially inserted into the cartridge holder 500 from the distal end 504 of the holder, cartridge coding features 414 fit into cartridge holder coding features 512, allowing cartridge 400 to continue its trajectory into cartridge holder 500. If the cartridge coding features 414 are not compatible and do not match cartridge holder coding features 512, the cartridge travel will be restricted, and the cartridge will not be able to continue to be inserted within cartridge holder.

Cartridge 400 may subsequently be removed from cartridge holder 500 by either manually disengaging clips 510, or through employment of a mechanism. Such a mechanism could be operated by rotating, partially or fully removing holder 500 from the injection device, or by some other means incorporated into the injection device itself. Pivot point features 514 on the interior of the clips 510 may be present, to allow the distal end of the clip to open as the pads 520 are pressed by the user, to manually disengage the clips from the snaps.

Figure 9:
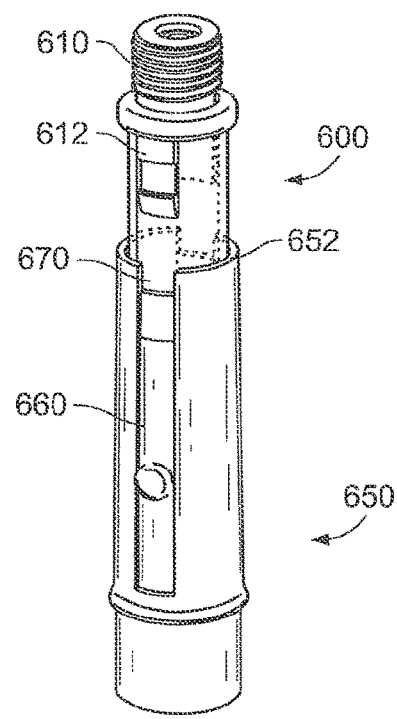
FIG. 9 illustrates a perspective view of an alternative exemplary arrangement of a cartridge and a cartridge holder.
Figure 10:
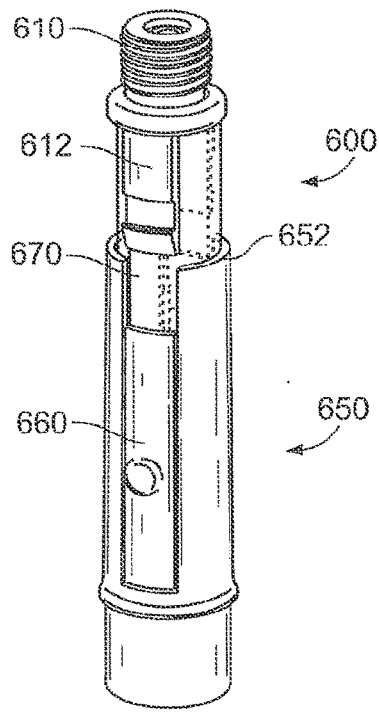
FIG. 10 illustrates a perspective view of another alternative exemplary arrangement of a cartridge and a cartridge holder.

FIGS. 9 and 10 illustrate perspective views of alternative arrangements of an exemplary cartridge 600 and a cartridge holder 650. In these arrangements, rather than having separate coding features at the distal end of the cartridge to correspond with coding features on the cartridge holder, clips 660 of cartridge holder 650 merely have varying widths or lengths. Cartridges 600 have retention caps 610 with snaps 612 that also vary in width or length. A cartridge that is designed to mate with a specific cartridge holder can thus only mate with that holder, due to the sizing of the clips and the snaps.

A comparison of the coding features and corresponding dedication features in FIGS. 9 and 10 shows some options for sizing of the features. For example, the snaps 612 in FIG. 9 have smaller widths than the snaps 612 of FIG. 10. Correspondingly, the slot 670 and clip 660 of the cartridge holder 650 in FIG. 9 have widths that match the snap width 612 of the cartridge of FIG. 9. Thus, the cartridge 600 in FIG. 9 can fit within slot 670 of FIG. 9. However, a cartridge with a wider width snap, such as the cartridge and snap in FIG. 10, could not fit within the holder slot of FIG. 9. FIG. 9 also shows how a clip can vary in length as well as width. Clip 660 extends further toward distal end 652 of cartridge holder 650 in FIG. 9 than the clip 660 shown in FIG. 10. Thus, snaps that are either too long or not long enough will not be able to allow for proper insertion of a cartridge that is mis-matched with an incorrect cartridge holder.

In this way, the coding features of the cartridge 600 are represented by the snaps 612 having a predetermined length and with. The corresponding coding features of the cartridge holder 650 are represented by the clips 660 and slots 670. The width and length of the snaps 612, clips 660 and slots 670 are adapted to each other such that each snap 612 slides in the corresponding slot 670 when the cartridge 600 travels axially within the cartridge holder 650 and a each snap 612 is in a snap-fit engagement with the corresponding clip 660 when the cartridge 600 is fully inserted in the cartridge holder 650, so that the cartridge assembly is in particular in the assembled position.

Figure 11:
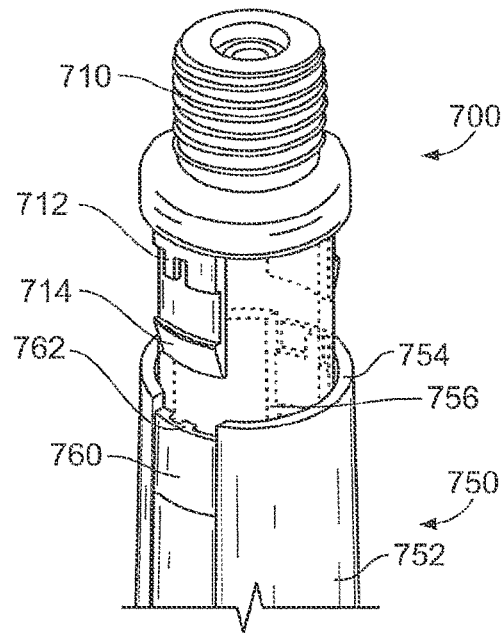
FIG. 11 illustrates a partial, perspective view of an alternative arrangement of a cartridge and a cartridge holder in an unlocked position.

FIG. 11 illustrates a partial, perspective view of an alternative arrangement of a cartridge 700 and a cartridge holder 750 in an unlocked position. Cartridge 700 comprises a retention cap 710 with radial coding features 712. Cartridge holder 750 comprises a main body 752 with a distal end 754, proximal end (not shown), and an aperture 756 at distal end 754. Cartridge holder 750 also comprises a plurality of retention clips 760 with radial coding features 762.

Cartridge 700 is axially inserted into distal end 754 of cartridge holder 750. In particular, cartridge 700 is inserted into the aperture 756, which, in this as well as in other embodiments, may have a diameter $D_1$ that is slightly greater than the diameter $D_2$ of the cartridge 700, as described in connection with FIGS. 1 and 2. Each of the coding features 712 has to be aligned with the corresponding cartridge holder coding features 762 in order to fully insert cartridge 700 within cartridge holder 750. Once aligned, the coding features 712 fit within the cartridge holder coding features 762, allowing snaps 714 to engage clips 760, and thus allowing the cartridge to be axially inserted within cartridge holder 750.

In particular, in this way a snap lock is formed by the respective clips 760 and corresponding snaps 714 carrying the coding features 712, 762 of the cartridge 700 and the cartridge holder 750. When the snap lock is in the locked position, the corresponding indents and protrusions of the coding features 712, 762 are in engagement with each other. Thus, the snap lock can only be brought in the locked position, in which locked position the cartridge is attached to the cartridge holder—preferably in a removable fashion— if the coding features of cartridge and cartridge holder match. When the snap lock is in the locked position, the cartridge assembly may be in the assembled position.

Figure 12:
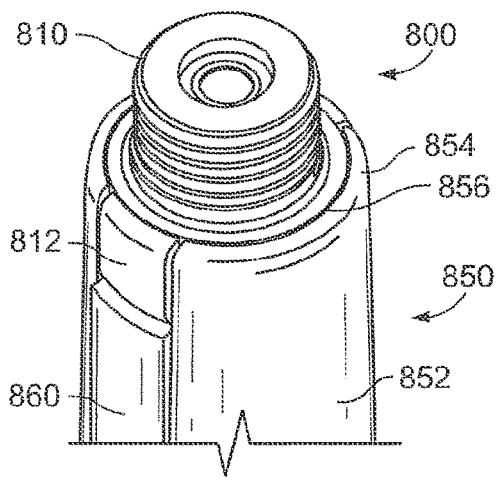
FIG. 12 illustrates the cartridge and cartridge holder of FIG. 11 in the locked position.
Figure 13:
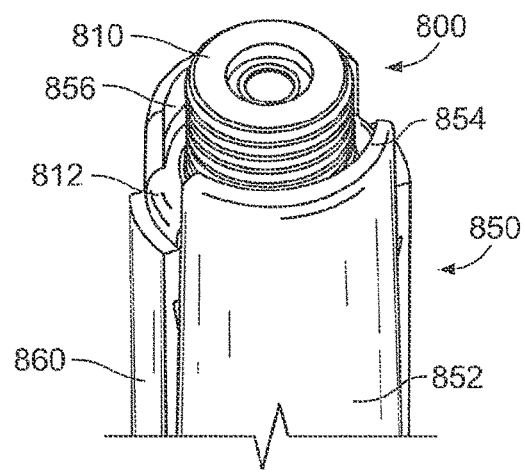
FIG. 13 illustrates the cartridge and cartridge holder of FIG. 11 in the removed position.

FIGS. 12 and 13 illustrate partial, perspective views of an alternative exemplary arrangement of a cartridge 800 and a cartridge holder 850. Cartridge 800 comprises a retention cap 810 with snaps 812. Cartridge holder 850 comprises a main body 852 with a distal end 854, a proximal end (not shown), and an aperture 856 at distal end 854. Cartridge holder 850 also comprises a plurality of retention clips 860.

Cartridge 800 is axially inserted into the aperture at distal end 854 of cartridge holder 850. Each of the snaps 812 has to be aligned with the corresponding retention clips 860 in order to fully insert cartridge 800 within cartridge holder 850. This retention cap 810 is designed such that cartridge 800 can subsequently be removed after a full insertion of cartridge 800 within cartridge holder 850. This is accomplished by pulling and disconnecting cartridge holder 850 away from the medical device, allowing cartridge 800 to axially pass entirely through cartridge holder 850. This movement of the cartridge holder 850 being pulled away over cartridge 800 is shown in FIG. 13. The clip 860 thus may act as a one-way gate, allowing snap 812 to pass through in one direction, but not to move back up in the opposite direction. This type of embodiment may lend itself to pen-resetting mechanisms where a lock nut interacts with the base of the holder, being reset as the holder is removed for cartridge removal, before then being replaced. Such pen-resetting mechanisms are, in principle, known to the person skilled in the art.

Figure 15:
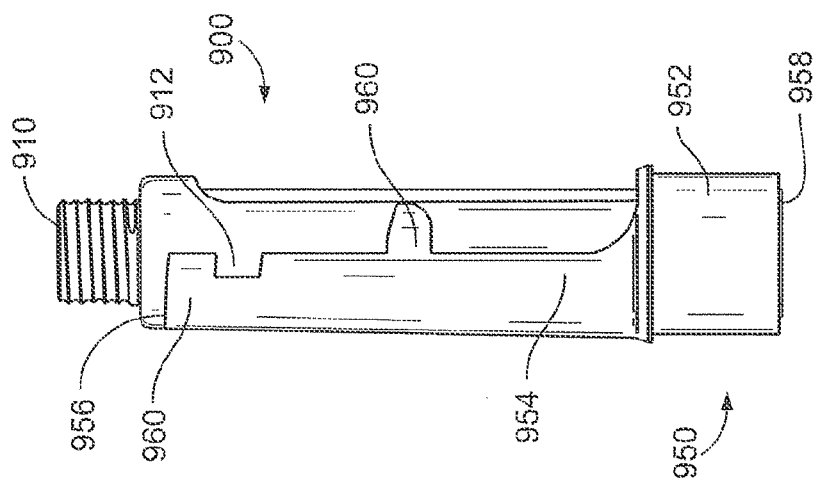
FIG. 15 illustrates a perspective view of the cartridge and cartridge holder of FIG. 14 in the affixed position.
Figure 14:
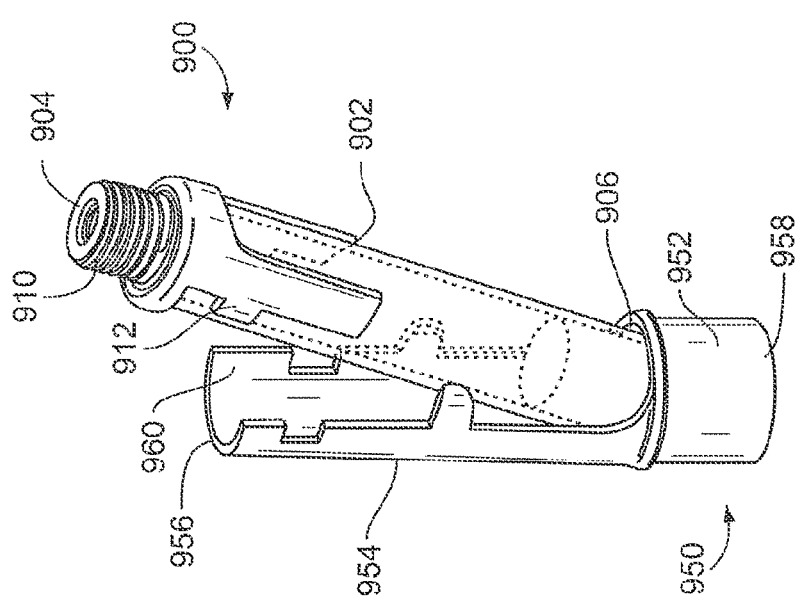
FIG. 14 illustrates a perspective view of an alternative exemplary arrangement of a cartridge and a cartridge holder.

FIGS. 14 and 15 illustrate another embodiment, in which a cartridge 900 is inserted obliquely into a cartridge holder 950. Cartridge 900 comprises a main body 902, a distal end 904, a proximal end 906, and a retention cap 910 with a plurality of coding features 912. Cartridge holder 950 comprises a cylindrical base 952 and a main body 954 with a distal end 956 and a proximal end 958. Main body 954 protrudes from base 952, ending at a top edge at distal end 956 and comprises an arc-shape extending along a portion of the circumference of base 952. In the present embodiment, the arc-shaped main body 954 has dedication or coding features 960 comprising either indents or protrusions along main body's side edges.

In use, cartridge 900 is inserted obliquely into holder 950, shown in FIG. 14. The coding features 912 on retention cap 910 of cartridge 900 are aligned with the corresponding coding features 960 on holder 950. As cartridge 900 is pushed into the arc-shaped main body of holder 950, cartridge coding features 912 fit within cartridge holder coding features 960, resulting in the affixed or assembled position shown in FIG. 15.

In the affixed position, an inner surface of the main body 954 in particular basically completely abuts the circumferential side surface of the cartridge 900. The exterior surface of the cartridge coding features 960 may extend the exterior surface of the main body 954 to form a generally smooth exterior surface, in particular without steps or kinks. The exterior surfaces are the surfaces facing away from the longitudinal axis of the cartridge in this case.

The cartridge coding features 912 must match the cartridge holder coding features 960 if the two components are to be successfully brought together. In this embodiment, it is the coding features themselves that hold the cartridge to the cartridge holder, in particular in the predetermined, assembled position of the cartridge assembly. If the coding features are not present, the cartridge will not be constrained in the distal direction.

Figure 18:
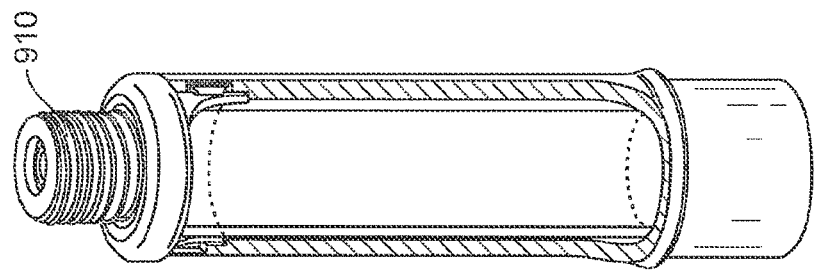
FIG. 18 illustrates a perspective view of the cartridge and cartridge holder of FIG. 16 in the locked position.
Figure 17:
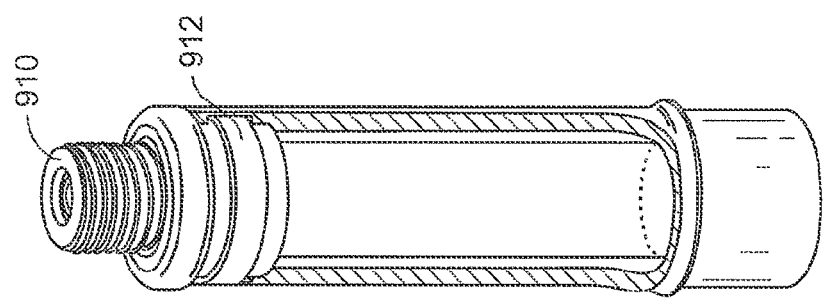
FIG. 17 illustrates a perspective view of the cartridge and cartridge holder of FIG. 16 in the partially assembled position.
Figure 16:
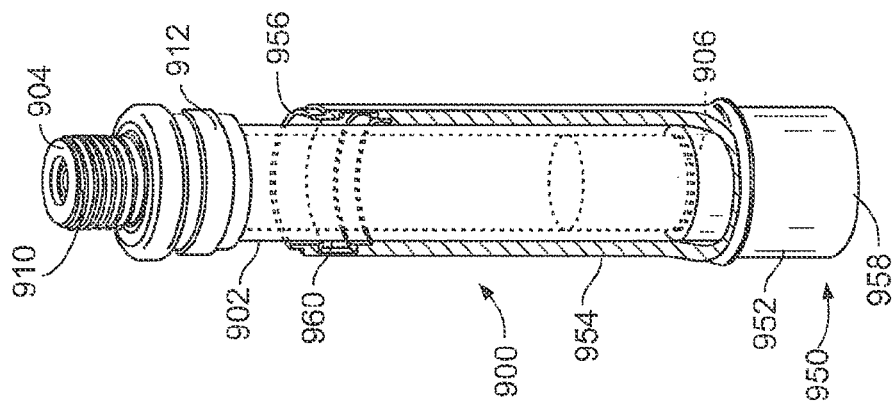
FIG. 16 illustrates a perspective view of an alternative exemplary arrangement of a cartridge and cartridge holder.

FIGS. 16, 17, and 18 illustrate a cartridge 900 and cartridge holder 950 with alternative features. Cartridge 900 comprises a main body 902, a distal end 904, proximal end 906, and a retention cap 910 with a coding feature 912, the coding feature 912 comprising a bayonet in the present embodiment. Cartridge holder 950 comprises a cylindrical base 952 and a main body 954 with a distal end 956 and a proximal end 958. Main body 954 protrudes from base 952, ending at a top edge at distal end 956. In one development, the main body may comprise an arc-shape extending along a portion of the circumference of base 952. In another development, the main body 954 has a tubular shape. The main body 954 has dedication or coding features 960 comprising grooves along the interior surface of the main body.

In use, the cartridge 900 is inserted axially into the distal end 956 of holder 950, from the position in FIG. 16 to the position in FIG. 17. Then, cartridge 900 is rotated, allowing bayonet 912 on the sleeve of retention cap 910 to engage with groove 960 on holder 950. This rotated, locked position is shown in FIG. 18 and represents in particular an assembled position of the cartridge assembly. When bayonet 912 is within groove 960, cartridge 900 is locked or retained within holder 950.

The size, position, or profile of bayonet 912 can be varied so as to provide distinct pairs of compatible cartridges and holders. For example, each drug may have its own distinct profile of a bayonet 912.

Those of skill in the art will recognize alternative geometries of these coding features may also be used. For example, the thickness or length of the coding mechanisms may be altered, and the gap may range in size as well. A change in any of these features may alter the force applied required to deform the coding mechanisms to affix them to the cartridge. More than one coding mechanism around the cartridge may be provided.

Although primarily aimed at the insulin market, the Applicants' presently proposed coding schemes may apply to other drugs. In fact, the Applicants' proposed coding mechanism may apply to any drug delivery device, with any type of reservoir or primary pack, e.g. inhaler, pouch. Standard parts may be used on devices for dispensing all drugs, and the coding applied. One advantage of the proposed coding mechanism allows for a coding method to the cartridge holder to prevent insertion of a cartridge into the incorrect holder.

Applicants' proposed coding mechanism results in a number of advantages. The coding mechanism assists a user to distinguish between medicaments, thereby helping to ensure that a delivery device can only be used with a medicament for which the device is intended. Therefore, with the coding system applied to the cartridge, the cartridge is prevented from being confused with any other drug by loading a cartridge with an incorrect or unwanted interface. Applicants' coded system prevents a user from fully attaching the cartridge assembly onto an incorrect dose setting mechanism. In addition, with Applicants' coding schemes, if a user attempts to load an incorrect cartridge assembly, the user will be alerted at an early stage of the assembly process.

Applicants' coding mechanism also results in a low cost mechanism since the mechanisms do not require a large number of parts and can be manufactured in a cost effective manner. Moreover, because of the ease of alteration of the coding features, there are quite a large number of different coding configurations between the holder and cartridge that may be used. Consequently, a large number of medicaments can be distinguished from one another.

With advantage, the cartridge coding features may be provided on a retention cap which is a separate piece, and is in particular manufactured separately from the main body of the cartridge. In this way, it is possible to manufacture the main body and charge it with the medicament on standard manufacturing systems, e.g. on manufacturing systems for generally tubular barrels, and to provide the cartridge with a coding feature corresponding to the respective medicament for the in a simple, subsequent step by attaching the respective retention cap to the main body.

Exemplary embodiments of the present invention have been described. Those skilled in the art will understand, however, that changes and modifications may be made to these arrangements without departing from the true scope and spirit of the present invention, which is in particular defined by the claims.

The invention claimed is:

1. A cartridge assembly for use with a drug delivery device, the cartridge assembly comprising:
   a cartridge holder designed for being connected with a drug delivery mechanism, the cartridge holder having a distal end and a proximal end;
   a cartridge having a distal end with a retention cap and a proximal end; and
   a snap lock with a snap and a clip for attachment of said cartridge with said cartridge holder, wherein one of the snap and the clip is comprised by the retention cap, and wherein the other one of the snap and the clip is comprised by the cartridge holder,
   wherein a main body of the cartridge is positionally fixed with respect to axial movement or with respect to axial and rotational movement by means of mechanical interaction of the retention cap with the cartridge holder,
   wherein the cartridge and the cartridge holder are configured to be fixed to each other in a predetermined rotational position, with the distal end of the cartridge holder being positioned adjacent the distal end of the cartridge,
   wherein said retention cap comprises at least one coding feature comprising axial protrusions, indents, or a combination thereof at a proximal end of the retention cap, and wherein the at least one coding feature is configured to affix said cartridge to said cartridge holder in the predetermined rotational position by mating of said at least one coding feature with a corresponding coding feature on said cartridge holder, wherein the corresponding coding feature comprises axial indents, protrusions, or a combination thereof at the distal end of said cartridge holder,
   wherein the predetermined rotational position is chosen out of one or two possible predetermined rotational positions,
   wherein the snap and the clip of the snap lock are unable to engage when the at least one coding feature of the retention cap does not fit within the corresponding coding feature of the cartridge holder,
   wherein the one of the snap and the clip comprised by the retention cap carries the at least one coding feature, and wherein the other one of the snap and the clip comprised by the cartridge holder carries the corresponding coding feature,
   wherein the snap comprises said at least one coding feature, and wherein an interior surface of the clip comprises the corresponding coding feature,
   wherein, when said cartridge is axially inserted into the distal end of said cartridge holder, the at least one coding feature mates with said corresponding coding feature, and
   wherein said snap attaches said cartridge to said cartridge holder in a removable fashion.

2. The cartridge assembly of claim 1, wherein the at least one coding feature and the corresponding coding feature form a locking mechanism of the cartridge assembly, and wherein the locking mechanism is configured to positionally fix the retention cap and the cartridge holder with respect to each other when the cartridge assembly is in an assembled position.

3. The cartridge assembly of claim 1, wherein said cartridge is axially inserted into an aperture at the distal end of said cartridge holder.

4. The cartridge assembly of claim 1, additionally comprising a lid, wherein,
   said cartridge comprises a clip,
   the lid is configured such that said clip of the cartridge remains visible when the lid is placed over the cartridge, and
   said cartridge holder comprises an aperture within which a protrusion on said clip of the cartridge fits to retain said cartridge within said cartridge holder.

5. The cartridge assembly of claim 1, wherein said cartridge is insertable into an aperture at the distal end of the cartridge holder, wherein the at least one coding feature mates with said corresponding coding feature, allowing said cartridge to fit within said cartridge holder.

6. The cartridge assembly of claim 1, wherein said snap is designed such that the cartridge is insertable into an aperture at the distal end of the cartridge holder and subsequently removable from said cartridge holder in a proximal direction, such that said cartridge slips through the proximal end of said cartridge holder, opposite of the distal end of the cartridge holder.

7. The cartridge assembly of claim 6 wherein, when a pulling or pushing force is applied for removal of the cartridge from said cartridge holder, said snap slides out of its attachment position.

8. The cartridge assembly of claim 1, wherein said cartridge holder comprises an arc-shaped main body extending from a cylindrical base.

9. The cartridge assembly of claim 8, wherein said cartridge is obliquely inserted into said cartridge holder by placing the proximal end of said cartridge on said base, and pressing said cartridge against said arc-shaped main body, and wherein, when said cartridge is pressed against said arc-shaped main body, said at least one coding feature on the retention cap mates with said corresponding coding feature.

10. The cartridge assembly of claim 8, wherein the-proximal end of said cartridge is axially inserted into said cartridge holder, until said proximal end of the cartridge rests on top of said cylindrical base.

11. The cartridge assembly of claim 10, wherein, after said cartridge is fully inserted into said cartridge holder, said at least one coding feature is rotated to fit within said corresponding coding feature, attaching said cartridge to said cartridge holder.

12. The cartridge assembly of claim 1, wherein the snap is designed such that the cartridge is insertable into an aperture at a distal end of the cartridge holder and said cartridge can subsequently be removed from said cartridge holder by a pulling force removing said cartridge holder from said cartridge, such that said cartridge slips through the distal end of said cartridge holder.

13. The cartridge assembly of claim 1, wherein:
the clip has a fixed end that is positionally fixed with respect to the retention cap and a free end that is radially displaceable with respect to the retention cap, or
the clip has a fixed end that is positionally fixed with respect to the cartridge holder and a free end that is radially displaceable with respect to the cartridge holder.

14. The cartridge assembly of claim 1, wherein the at least one coding feature and the corresponding coding feature comprise at least one pair of clips and snaps and wherein the snaps and the clips, respectively, of each pair of the snaps and clips have mutually different widths and/or lengths.

15. A cartridge assembly for use with a drug delivery device, the cartridge assembly comprising:
a cartridge holder designed for being connected with a drug delivery mechanism, the cartridge holder having a distal end and a proximal end;
a cartridge having a distal end with a retention cap and a proximal end; and
a snap lock with a snap and a clip for attachment of said cartridge with said cartridge holder, wherein one of the snap and the clip is comprised by the retention cap and wherein the other one of the snap and the clip is comprised by the cartridge holder,
wherein a main body of the cartridge is positionally fixed with respect to axial movement or with respect to axial and rotational movement by means of mechanical interaction of the retention cap with the cartridge holder,
wherein the cartridge and the cartridge holder are configured to be fixed to each other in a predetermined rotational position, with the distal end of the cartridge holder being positioned adjacent the distal end of the cartridge,
wherein said retention cap comprises at least one coding feature comprising circumferential protrusions, indents, or a combination thereof and wherein the at least one coding feature is configured to affix said cartridge to said cartridge holder in the predetermined rotational position by mating of said at least one coding feature with a corresponding coding feature on said cartridge holder, wherein the corresponding coding feature comprises circumferential indents, protrusions, or a combination thereof,
wherein the predetermined rotational position is chosen out of one or two possible predetermined rotational positions,
wherein the snap and the clip of the snap lock are unable to engage when the at least one coding feature of the retention cap does not fit within the corresponding coding feature of the cartridge holder, and wherein said cartridge holder comprises an arc-shaped main body extending from a cylindrical base, and
wherein said cartridge is obliquely inserted into said cartridge holder by placing the proximal end of said cartridge on said base, and pressing said cartridge against said arc-shaped main body, and wherein, when said cartridge is pressed against said arc-shaped main body, said at least one coding feature on the retention cap mates with said corresponding coding feature.

16. A cartridge assembly for use with a drug delivery device, the cartridge assembly comprising:
a cartridge holder designed for being connected with a drug delivery mechanism, the cartridge holder having a distal end and a proximal end;
a cartridge having a distal end with a retention cap and a proximal end; and
a snap lock with a snap and a clip for attachment of said cartridge with said cartridge holder, wherein one of the snap and the clip is comprised by the retention cap and wherein the other one of the snap and the clip is comprised by the cartridge holder,
wherein a main body of the cartridge is positionally fixed with respect to axial movement or with respect to axial and rotational movement by means of mechanical interaction of the retention cap with the cartridge holder;
wherein the cartridge and the cartridge holder are configured to be fixed to each other in a predetermined rotational position, with the distal end of the cartridge holder being positioned adjacent the distal end of the cartridge; and
said retention cap comprises at least one coding feature comprising axial protrusions, indents, or a combination thereof at a proximal end of the retention cap and wherein the at least one coding feature is configured to affix said cartridge to said cartridge holder in the predetermined rotational position by mating of said at least one coding feature with a corresponding coding feature on said cartridge holder, wherein the corresponding coding feature comprises axial indents, protrusions, or a combination thereof at the distal end of said cartridge holder,
wherein the predetermined rotational position is chosen out of one or two possible predetermined rotational positions,
wherein the snap and the clip of the snap lock are unable to engage when the at least one coding feature of the retention cap does not fit within the corresponding coding feature of the cartridge holder,
wherein the snap of the snap lock is designed such that the cartridge is insertable into an aperture at a distal end of the cartridge holder and said cartridge can subsequently be removed from said cartridge holder by a pulling force removing said cartridge holder from said cartridge, such that said cartridge slips through the distal end of said cartridge holder.

* * * * *